United States Patent
Young

(10) Patent No.: US 7,699,874 B2
(45) Date of Patent: Apr. 20, 2010

(54) LOW PROFILE SPINAL ROD CONNECTOR SYSTEM

(75) Inventor: John Stewart Young, Memphis, TN (US)

(73) Assignee: Warsaw Orthopedic, Inc.

( * ) Notice: Subject to any disclaimer, the term of this patent is extended or adjusted under 35 U.S.C. 154(b) by 668 days.

(21) Appl. No.: 11/365,365

(22) Filed: Mar. 1, 2006

(65) Prior Publication Data

US 2007/0233070 A1    Oct. 4, 2007

(51) Int. Cl.
*A61B 17/70*    (2006.01)

(52) U.S. Cl. .................. 606/250; 606/280; 606/71; 606/277

(58) Field of Classification Search .......... 606/280, 606/70, 71, 276, 277, 278, 59, 260, 259, 606/250, 54, 55, 56, 57, 281, 282, 283, 284, 606/285, 286, 287, 288, 289, 290, 291, 292, 606/293, 294, 295, 296, 297, 298, 299, 246, 606/251, 252, 253, 254, 255, 256, 257, 258, 606/261, 262, 263, 264, 265, 279; 439/781, 439/783

See application file for complete search history.

(56) References Cited

U.S. PATENT DOCUMENTS

| | | | |
|---|---|---|---|
| 3,900,025 A * | 8/1975 | Barnes, Jr. .................. | 606/71 |
| 4,361,141 A | 11/1982 | Tanner | |
| 4,771,767 A | 9/1988 | Steffee | |
| 4,773,402 A | 9/1988 | Asher et al. | |
| 4,854,304 A | 8/1989 | Zielke | |
| 4,929,247 A * | 5/1990 | Rayhack .................. | 606/53 |
| 5,053,034 A | 10/1991 | Olerud | |
| 5,154,718 A | 10/1992 | Cozad et al. | |
| 5,217,461 A | 6/1993 | Asher et al. | |
| 5,330,472 A | 7/1994 | Metz-Stavenhagen | |
| 5,330,474 A | 7/1994 | Lin | |
| 5,336,223 A | 8/1994 | Rogers | |
| 5,403,314 A | 4/1995 | Currier | |
| 5,425,732 A | 6/1995 | Ulrich | |
| 5,486,174 A | 1/1996 | Fournet-Fayard et al. | |
| 5,487,744 A | 1/1996 | Howland | |
| 5,562,660 A | 10/1996 | Grob | |
| 5,575,790 A | 11/1996 | Chen et al. | |
| 5,593,408 A | 1/1997 | Gayet et al. | |
| 5,630,816 A | 5/1997 | Kambin | |
| 5,643,260 A | 7/1997 | Doherty | |
| 5,658,284 A | 8/1997 | Sebastian et al. | |
| 5,993,449 A | 11/1999 | Schlapfer et al. | |
| 6,099,528 A | 8/2000 | Saurat | |

(Continued)

FOREIGN PATENT DOCUMENTS

EP    0 612 507 A1    2/1994

(Continued)

*Primary Examiner*—Eduardo C Robert
*Assistant Examiner*—Jan Christopher Merene

(57) ABSTRACT

A spinal rod system includes a first rod and a second rod engaged to a connector with the first and second rods extending axially therefrom in opposite direction and in laterally offset relation. The connector includes first and second side-by-side receptacles for receiving respective ones of the rods. The connector includes a clamping arrangement to releasably secure the rods in the respective receptacles. The receptacles allow the relative axial position between the rods to be adjusted to accommodate anatomical conditions.

17 Claims, 2 Drawing Sheets

U.S. PATENT DOCUMENTS

| | | | |
|---|---|---|---|
| 6,102,912 | A | 8/2000 | Cazin et al. |
| 6,106,527 | A | 8/2000 | Wu et al. |
| 6,117,135 | A * | 9/2000 | Schlapfer .................... 606/250 |
| 6,136,002 | A * | 10/2000 | Shih et al. .................... 606/250 |
| 6,171,311 | B1 | 1/2001 | Richelsoph |
| 6,241,730 | B1 | 6/2001 | Alby |
| 6,328,739 | B1 | 12/2001 | Liu et al. |
| 6,328,741 | B1 | 12/2001 | Richelsoph |
| 6,520,962 | B1 | 2/2003 | Taylor et al. |
| 6,676,661 | B1 | 1/2004 | Benlloch et al. |
| 6,685,705 | B1 | 2/2004 | Taylor |
| 6,749,612 | B1 * | 6/2004 | Conchy et al. .............. 606/250 |
| 2002/0111625 | A1 | 8/2002 | Richelsoph et al. |
| 2004/0204713 | A1 * | 10/2004 | Abdou ........................ 606/71 |
| 2004/0220575 | A1 | 11/2004 | Biedermann et al. |
| 2005/0004573 | A1 * | 1/2005 | Abdou ........................ 606/61 |
| 2005/0154388 | A1 | 7/2005 | Roussouly et al. |
| 2005/0171537 | A1 | 8/2005 | Mazel et al. |
| 2005/0228376 | A1 | 10/2005 | Boomer et al. |
| 2005/0228378 | A1 | 10/2005 | Kalfas et al. |
| 2005/0277925 | A1 | 12/2005 | Mujwid |
| 2005/0277932 | A1 | 12/2005 | Farris |
| 2006/0217724 | A1 * | 9/2006 | Suh et al. ....................... 606/71 |
| 2006/0235398 | A1 * | 10/2006 | Farris et al. ................... 606/69 |
| 2006/0235405 | A1 * | 10/2006 | Hawkes ....................... 606/69 |
| 2007/0185489 | A1 * | 8/2007 | Abdou ........................ 606/61 |
| 2007/0293864 | A1 * | 12/2007 | Reimels et al. ............... 606/69 |

FOREIGN PATENT DOCUMENTS

| | | |
|---|---|---|
| EP | 0 584 803 A1 | 3/1994 |
| WO | WO 01/91656 | 12/2001 |

\* cited by examiner

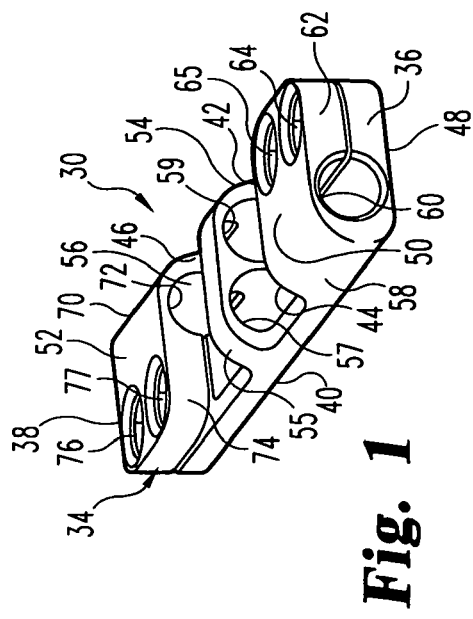

LOW PROFILE SPINAL ROD CONNECTOR SYSTEM

BACKGROUND

The spine is subject to various pathologies that compromise its load bearing and support capabilities. Such pathologies of the spine include, for example, degenerative diseases, the effects of tumors and, of course, fractures and dislocations attributable to physical trauma. In the treatment of diseases, malformations or injuries affecting spinal motion segments (which include two or more adjacent vertebrae and the disc tissue or disc space therebetween), and especially those affecting disc tissue, it has long been known to remove some or all of a degenerated, ruptured or otherwise failing disc. It is also known that artificial discs, fusion implants, or other interbody devices can be placed into the disc space after disc material removal. External stabilization of spinal segments alone or in combination with interbody devices also provides advantages. Elongated rigid plates, rods and other external stabilization devices have been helpful in the stabilization and fixation of a spinal motion segment, in correcting abnormal curvatures and alignments of the spinal column, and for treatment of other conditions.

While external rod systems have been employed along the vertebrae, the geometric and dimensional features of these rod systems and patient anatomy constrain the surgeon during surgery and prevent optimal placement and attachment along the spinal column. For example, elongated, one-piece rods can be difficult to maneuver into position along the spinal column, and also provide the surgeon with only limited options in sizing and selection of the rod system to be placed during surgery. Accommodation of post-operative anatomical changes in the patient can also present challenges.

SUMMARY

In one aspect, a rod system includes a rod connector having a first receptacle axially receiving a first rod and a first clamping arm movable relative the rod to clampingly engage the first rod to the connector and a second receptacle axially receiving a second rod and a second clamping portion movable relative to the second rod to clampingly engage the second rod in the connector. The connector can be configured with the receptacles extending axially along opposites sides of a central axis of the connector body and in side-by-side relation.

According to another aspect, a spinal rod system includes a connector and first and second spinal rods clampingly engaged to the connector and extending in opposite directions from the connector in laterally offset relation. The connector includes an elongate body extending along a central longitudinal axis between a first end and a second end. The body includes a bottom member extending between the first and second ends and a first clamping arm adjacent the first end defining a first receptacle with the bottom member and a second clamping arm adjacent the second end defining a second receptacle with the bottom member. The first receptacle extends along a first longitudinal axis offset to a first side of the central longitudinal axis and the second receptacle extends along a second longitudinal axis offset to a second side of the central longitudinal axis opposite the first side.

According to another aspect, a spinal rod system includes a connector and first and second spinal rods clampingly engaged to the connector and extending in opposite directions from the connector in laterally offset relation. The connector includes an elongate body extending along a central longitudinal axis between a first end and a second end. The body includes a bottom member extending between the first and second ends and a first clamping arm adjacent the first end defining a first receptacle with the bottom member for receiving the first rod. A second clamping arm adjacent the second end defines a second receptacle with the bottom member for receiving the second rod. The first and second clamping arms each include a first end portion extending from the respective first and second receptacles along the bottom member and a pair of engaging members extending through each of the end portions and engaging the bottom member. The first pair of engaging members for the first clamping arm are aligned along a first axis offset to a first side of the central longitudinal axis, and a second pair of engaging members for the second clamping arm are aligned along a second axis offset to a second side of the central longitudinal axis.

According to another aspect, a spinal rod system includes a connector and first and second spinal rods clampingly engaged to the connector and extending in opposite directions from the connector in laterally offset relation. The connector includes a bottom member extending between the first and second ends and between opposite sides of a body of the connector. The body also includes a first clamping arm adjacent the first end defining a first receptacle with the bottom member that extends along a first longitudinal axis offset to a first side of the central longitudinal axis. The body further includes a second clamping arm adjacent the second end defining a second receptacle with the bottom member that extends along a second longitudinal axis offset to a second side of the central longitudinal axis. The body includes a medial member extending between the opposite sides of the body with the first and second receptacles extending through the medial member. A first window is between the medial member and the first clamping arm in communication with the first and second receptacles. A second window is between the medial member and the second clamping arm in communication with the first and second receptacles.

These and other aspects will be apparent from the description that follows.

BRIEF DESCRIPTION OF THE FIGURES

FIG. 1 is a perspective view of a rod connector.

FIG. 2 is an end elevation view of the rod connector of FIG. 1.

FIG. 3 is a plan view of the rod connector with first and second rods received thereby and engaging members engaged to the connector.

FIG. 4 is an elevation view of the connector and rods of FIG. 3 positioned along and anchored to a spinal column motion segment with the motion segment and anchors shown diagrammatically.

DESCRIPTION OF THE ILLUSTRATED EMBODIMENTS

Figure 5:
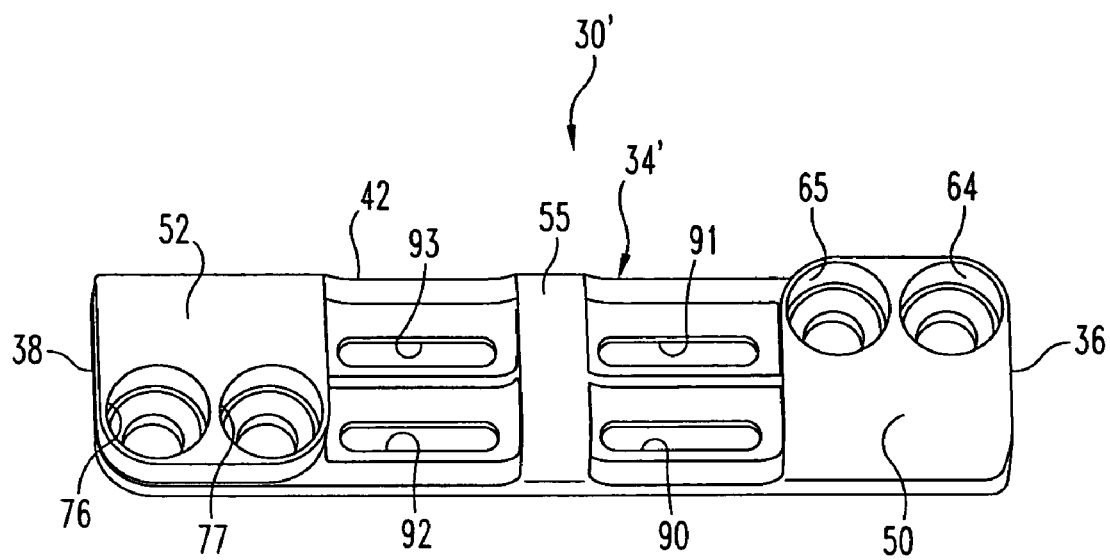
FIG. 5 is a perspective of another embodiment rod connector.

For the purposes of promoting an understanding of the principles of the invention, reference will now be made to the embodiments illustrated in the drawings and specific language will be used to describe the same. It will nevertheless be understood that no limitation of the scope of the invention is hereby intended. Any such alterations and further modifications in the illustrated devices, and any such further applications of the principles of the invention as illustrated herein are contemplated as would normally occur to one skilled in the art to which the invention relates.

In FIGS. 1 and 2 there is shown a rod connector 30 for engaging a pair of rods in offset relation to one another along a spinal column. The rods can extend in opposite directions from rod connector 30 for positioning along one or more spinal motion segments of the spinal column to provide stabilization. The positioning of the rods in rod connector 30 can be readily adjusted to accommodate a change in spacing between anchors engaged along the spinal column.

For example, in FIGS. 3 and 4 there is shown a spinal rod system 10 including a first rod 12 and a second rod 22. First rod 12 and second rod 22 are releasably coupled with rod connector 30 in laterally offset and axially extending relation. Furthermore, first rod 12 can be secured to at least one vertebra V1 with at least one first anchor 14, and second rod 22 can be secured to at least one second vertebra V2 with at least one second anchor 24. The length of the construct between anchors 14, 24 can be decreased or increased by adjusting the positioning of one or more of the rods 12, 22 in rod connector 30. Such adjustment may be desirable, for example, to provide an optimal fit during surgery or to adjust the length of the construct as a result of growth or other changes in the patient anatomy after the initial implantation procedure.

Connector 30 includes a connector body 34 releasably engageable to each of the first and second rods 12, 22. The connector 30 is configured to secure rods 12, 22 to one another in axially extending, offset relation to one another while minimizing the footprint or intrusiveness of the connector into the tissue surrounding the rod system and allowing the length of the rod construct for positioning and/or attachment along the spinal column to be readily adjustable.

Body 34 includes extends along a central longitudinal axis 32 between a first end 36 and an opposite second end 38. Body 34 also includes a first side 40 extending along a first side of central longitudinal axis 32 and an opposite second side 42 extending along a second side of central longitudinal axis 32 opposite first side 40. Body 34 includes a first receptacle 44 extending along and offset to the first side of central longitudinal axis 32, and a second receptacle 46 extending along and offset to the second side of central longitudinal axis 32. First and second receptacles 44, 46 extend along and are defined at least in part by a plate-like bottom member 48 of body 34.

Body 34 further includes a first clamping arm 50 extending from bottom member 48 about a portion of first receptacle 44 adjacent first end 36. Body 34 also includes a second clamping arm 52 extending from bottom member 48 about a portion of second receptacle 46 adjacent second end 38. Body 34 includes a medial member 55 extending between first and second sides 40, 42. First and second receptacles 44, 46 extend through medial member 50 and are at least in part defined by recessed portions 57, 59 of medial member 55 oriented toward bottom member 48.

Body 34 also includes a first window 54 defined between medial member 55 and first clamping arm 50, and a second window 56 defined between medial member 55 and clamping arm 52. Windows 54, 56 are each in communication with respective portions of each of the first and second receptacles 44, 46. Windows 54, 56 allow visualization of rods 12, 22 in receptacles 44, 46 and reduce the material thickness along at least a portion of body 34 to reduce resistance to bending.

First clamping arm 50 includes a rounded connecting portion 58 integrally formed with bottom member 48 along first side 40 of body 34. Clamping arm 50 includes a recessed portion 60 extending about first receptacle 44 to an end portion 62. End portion 62 extends along bottom member 48 from first receptacle 44 to second side 42. End portion 62 is movable toward and away from bottom member 48 by bending connecting portion 58 to selectively clamp and release first rod 12 in first receptacle 44. End portion 62 further provides an abutment at the terminal end of second receptacle 46.

End portion 62 can include bores 64, 65 extending therethrough that are aligned with bores 84, 85 (FIGS. 5-6) in bottom member 48. Bores 64, 65 are aligned along second longitudinal axis 23 and extend transversely thereto. Engaging members 68, 69 are positionable in respective ones of the bores 64, 65 to engage the aligned bores in bottom member 48 and engage end portion 62 against bottom member 48, firmly clamping first rod 12 in first receptacle 44. Engaging members 68, 69 can be threaded to threadingly engage internal threads along the respective bores 84, 85, 86, 87 in bottom member 48, and can include an enlarged head to contact end member 62 adjacent its upper surface to provide a clamping effect. Bores 64, 65 can include a flared or recessed portion adjacent the upper surface of end portion 62 to recess the head of the respective engaging member 68, 69 adjacent to or below the upper surface, minimizing the overall height of the construct.

Second clamping arm 52 includes a rounded connecting portion 70 integrally formed with bottom member 48 along second side 42 of body 34. Clamping arm 52 includes a recessed portion 72 extending about second receptacle 46 to an end member 74. End member 74 extends along bottom member 48 from second receptacle 46 to first side 40, and is movable toward and away from bottom member 48 about end 70 to selectively clamp and release second rod 22 in second receptacle 46. End member 74 further provides an abutment at the terminal end of first receptacle 44.

End member 74 can include bores 76, 77 extending therethrough that are aligned with bores 86, 87 (FIGS. 5-6) in bottom member 48. Bores 76, 77 are aligned along first longitudinal axis 13 and extend transversely thereto. Engaging members 78, 79 are positionable in respective ones of the bores 76, 77 to engage the aligned bores in bottom member 48 and engage end member 74 against bottom member 48, firmly clamping second rod 22 in second receptacle 46. Engaging members 78, 79 can be threaded to threadingly engage internal threads along the respective bores in bottom member 48 and include an enlarged head to contact end member 74 adjacent its upper surface to provide a clamping effect. Bores 76, 77 can include a flared or recessed portion adjacent the upper surface of end member 74 to recess the head of the respective engaging member 78, 79 adjacent to or below the upper surface, minimizing the overall height of the construct.

First and second receptacles 44, 46 can include bottom portions defined at least in part by recessed portions extending along axes 13, 23 and opening toward the upper surface of connector 30. Upper portions of the receptacles 44, 46 capture the rods 12, 22 therein, and can be defined at least in part by the underside of clamping arms 50, 52 and medial member 55. The recessed portions in isolation can define a semi-cylindrical shape and together define a cylindrical shape to correspond to the outer shape of a cylindrical rod. Other shapes for the recessed portions and rods are also contemplated. In the illustrated embodiment, the recessed portions along bottom member 48 extend along the entire length of the respective receptacles 44, 46 from the respective first and second end 36, 38 to the opposite terminal end.

First rod 12 and second rod 22 can each include an elongated body extending axially from a first end received in the respective receptacles 44, 46 to an opposite second end (not shown.) The length of rods 12, 22 can be selected to extend along one, two, three or more spinal motion segments from the respective ends 36, 38 of connector 30. One or more anchors 14, 24 can be engaged to the rods 12, 22 at various locations along their respective lengths to secure rods 12, 22 to one or more vertebrae. One or both of the ends of each of the rods 12, 22 may include a coupling member, a coupling body, or provide a terminal end shaped like the corresponding rod along its length.

As shown in FIG. 3, first rod 12 extends along longitudinal axis 13 when positioned in first receptacle 44, and second rod 22 extends along a longitudinal axis 23 when positioned in second receptacle 46. Since the longitudinal axes 13, 23 are offset from one another on opposite sides of central longitudinal axis 32, rods 12, 22 can overlap one another in a lengthwise direction in connector 30. Accordingly the length of connector 30 between first and second ends 36, 38 can be minimized along with its intrusion into the surrounding tissue while providing maximum adjustability in the overall length of the rod construct extending along the spinal column.

As shown in FIG. 4, windows 54, 56 provide an area along the mid-portion of connector 30 of less material thickness. This can facilitate bending of connector 30 to contour it along the anatomy of the patient during implantation. Medial member 55 can receive the ends of the rods 12, 22 in receptacles 44, 46 and prevent the rods from jutting or splaying outwardly into the adjacent tissue when connector 30 is bent or flexed.

As shown in FIGS. 1, 2 and 4, the overall height of the connector 30 is reduced by providing engaging members that directly engage bottom member 48 rather than by directly contacting rods 12, 22 with engaging members through the upper surface of the arms 50, 52. Offsetting the engaging members to the opposite side of the receptacle in which the rod is positioned allows the top-loading capability of the engaging members into the connector to be maintained, facilitating access in subsequent surgical procedures while allowing the height of connector 30 to be minimized.

Figure 6:
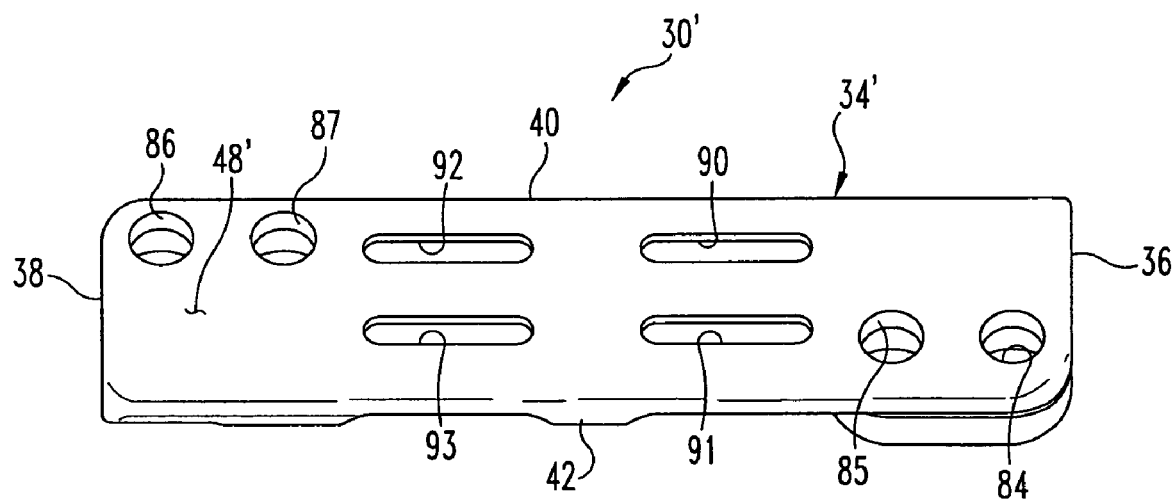
FIG. 6 is a perspective view looking toward the bottom member of the rod connector of FIG. 5.

Another embodiment rod connector 30' is shown in FIGS. 5 and 6. Rod connector 30' is substantially similar to rod connector 30, and like elements are designated with the same reference numerals. Rod connector 30' includes a body 34' having a number of windows extending through bottom member 48'. Specifically, a first elongate window 90 is located in communication with first receptacle 44 on one side of medial member 55, and a second elongate window 92 is located in communication with first receptacle 44 on the other side of medial member 55. In addition, a third elongate window 91 is located in communication with second receptacle 46 on one side of medial member 55, and a fourth elongate window 93 is located in communication with second receptacle 46 on the other side of medial member 55.

Windows 90, 91, 92, 93 facilitate surgeon visualization of the location of the rod in the respective receptacles 44, 46. For the purposes of revision surgery, the surgeon can determine the length of each rod available along connector 30' at a particular end of the connector 30' to adjust the length of the construct between anchors. If the necessary length is available at one of the ends of connector 30', then access to one of the ends is all that is necessary to revise the length of the construct, reducing the length of revision incision and potential implant and trauma on the patient. Rods 12, 22 can be of the same size, shape and material properties, or more have one or more of these characteristics that differ from one another. Connector 30 allows rods of differing characteristics to be secured to one another in laterally offset and axially extending relation for positioning along multiple levels of the spinal column and provide a rod system that is adapted for the anatomy, surgical condition, or surgical procedure. In one embodiment, the characteristics include differing cross-sectional dimensions of the rods 12, 22. Other embodiments contemplate selection criteria for selection and assembly of the rods to include any one or combination of characteristics, including length, contouring, flexibility, surface features, shape, section modulus, elasticity, materials and material properties, and coatings, for example.

In one specific application, the diameter of rod 12 is sized to extend along a first portion of the spine, such as the cervical region, and the diameter of second rod 22 is sized to extend along a second portion of the spine, such as the thoracic region. Other systems contemplate multiple rods coupled to one another in axially offset fashion with characteristics adapted for positioning along any one or combination of the sacral, lumbar, thoracic and cervical regions of the spinal column.

Connector 30 is configured to be secured to rods 12, 22 with rods 12, 22 in side-by-side or near side-by-side relation. When in side-by-side relation, rods 12, 22 can overlap one another in connector 30 in a lengthwise direction. This minimizes the footprint or intrusiveness of connector 30 into the tissue surrounding the rod system, and maximizes the length of the rod portion of each rod available for positioning and/or attachment along the spinal column. The positioning of rods 12, 22 in connector 30 can also be adjusted so that the rods 12, 22 do not directly overlap one another, but rather the end of rod 12 is positioned in window 54 and the end of rod 22 is positioned in window 56.

In the embodiments illustrated herein, although only one connector is shown, one or more of the first and second rods can be adapted for engagement with another rod with another connector 30 or other device at each end thereof so that three or more rods may comprise the rod system. The rods can be secured to vertebrae of the spinal column system with any one or combination of hooks, screws, bolts, multi-axial screws, staples, cables or wires, sutures, clamps, and/or other attachment devices and systems, with or without interbody fusion devices or implants between vertebrae.

Engaging members 68, 69, 78, 79 can be positionable in the respective bores of connector 30 either prior to placement of rods 12, 22 in receptacles 44, 46 or after placement. The engaging members can be in the form of set screws with a proximally oriented tool engaging recess to facilitate engagement with a driving tool. Other embodiments contemplate other arrangements for connector 30 and the engaging members. For example, the engaging members can be a stud or pin that is received in a hole or recess in connector 30, and a nut engaged thereto to engage connector 30 in clamping engagement with the rods 12, 22. The engaging members can include a bayonet locking type device or other suitable engagement relationship.

While the invention has been illustrated and described in detail in the drawings and foregoing description, the same is to be considered as illustrative and not restrictive in character. All changes and modifications that come within the spirit of the invention are desired to be protected.

What is claimed is:

1. A spinal rod system, comprising: a connector including an elongate body extending along a central longitudinal axis between a first end and a second end, said body including a bottom member extending between said first and second ends and a first clamping arm adjacent said first end defining a first receptacle with said bottom member and a second clamping arm adjacent said second end defining a second receptacle with said bottom member, said first receptacle extending along a first longitudinal axis offset to a first side of said central longitudinal axis and said second receptacle extending along a second longitudinal axis offset to a second side of said central longitudinal axis opposite said first side;

a first elongated rod extending between a first end and an opposite second end, said first rod end-being axially received in said first receptacle of said connector along said first longitudinal axis with said first rod extending from said first end of said body in a direction away from said second end, said first clamping arm being bendable relative to said bottom member and around said first receptacle for engagement against said bottom member to clampingly engage said first rod in said first receptacle with said first clamping arm; and a second elongated rod extending between a first end and an opposite second end, said second rod being axially received in said second receptacle of said connector along said second longitudinal axis with said second rod extending from said second end of said body in a direction away from said first end and being clampingly engaged in said second receptacle with said second clamping arm, wherein said body includes a medial member extending from said bottom member and between first and second sides of said body, said first and second receptacles extending through said medial member.

2. The system of claim 1, wherein said body defines a first window opening into said first and second receptacles between said medial member and said first clamping arm and a second window opening into said first and second receptacles between said medial member and said second clamping arm.

3. The system of claim 2, wherein:
said first clamping arm includes a connecting portion on said first side extending from said bottom member to a recessed portion extending about said first receptacle; and
said second clamping arm includes a connecting portion on said second side extending from said bottom member to a recessed portion extending about said second receptacle.

4. The system of claim 3, wherein said first clamping arm includes an end portion extending from said recessed portion of said first clamping arm along said bottom member toward said second side of said connector and said second clamping arm includes an end portion extending from said recessed portion of said second clamping arm along said bottom member toward said first side of said connector, wherein said end portion of said first clamping arm forms a terminal end of said second receptacle between said first window and said first end of said body and said end portion of said second clamping arm forms a terminal end of said first receptacle between said second window and said second end of said body.

5. The system of claim 4, wherein said end portions of each of said first and second clamping arms are movable about said connecting portion thereof toward said bottom member to clampingly engage said respective first and second rod in said respective first and second receptacle.

6. The system of claim 5, wherein:
said end portion of said first clamping arm includes a pair of bores aligned along and extending transversely to said second longitudinal axis and engaging members in said bores threadingly engaged with said bottom member; and
said end portion of said second clamping arm includes a pair of bores aligned along and extending transversely to said first axis and engaging members in said bores threadingly engaged with said bottom member.

7. The system of claim 3, wherein said bottom member and said recessed portion of each of said clamping arms define a cylindrical shape along each of said respective receptacles.

8. The system of claim 1, wherein said bottom member includes a first semi-cylindrical recess extending along said first receptacle and a second semi-cylindrical recess extending along said second receptacle.

9. A spinal rod system, comprising: a connector including an elongate body extending along a central longitudinal axis between a first end and a second end, said body including a bottom member extending between said first and second ends and a first clamping arm adjacent said first end defining a first receptacle with said bottom member and a second clamping arm adjacent said second end defining a second receptacle with said bottom member, wherein:

said first clamping arm includes a first end portion extending from said first receptacle along said bottom member, said first end portion including a first pair of engaging members extending therethrough and engaging said bottom member, said first pair of engaging members being aligned along a first longitudinal axis offset to a first side of said central longitudinal axis;

said second clamping arm including a second end portion extending from said second receptacle along said bottom member, said second end portion including a second pair of engaging members extending therethrough and engaging said bottom member, said second pair of engaging members being aligned along a second longitudinal axis offset to a second side of said central longitudinal axis;

a first elongated rod received in said first receptacle of said connector and being clampingly engaged therein with said first clamping arm with said first rod including a first end positioned in one of said first and second receptacles and extending from said first end of said first rod away from said second end of said body and outwardly from said first end of said body; and a second elongated rod received in said second receptacle of said connector and being clampingly engaged therein with said second clamping arm with said second rod including a first end positioned in one of said first and second receptacles and extending from said first end of said second rod away from said first end of said body and outwardly from said second end of said body, wherein said first receptacle extends along said second longitudinal axis and said second receptacle extends along said first longitudinal axis, wherein said first and second longitudinal axes are parallel to one another and are parallel to said central longitudinal axis.

10. The system of claim 9, wherein said engaging members are set screws threadingly engaged at least with said bottom member.

11. The system of claim 9, wherein:
said bottom member includes a first recessed portion and said first clamping arm includes a recessed portion aligned with and opposite said first recessed portion to define at least a portion of said first receptacle; and
said bottom member includes a second recessed portion and said second clamping arm includes a recessed portion aligned with and opposite said second recessed portion to define at least a portion of said second receptacle.

12. The system of claim 11, wherein:
said first recessed portion forms a semi-cylindrical shape extending along said second longitudinal axis from said first end of said bottom member to said second clamping arm; and said second recessed portion forms a semi-cylindrical shape extending along said first longitudinal axis from said second end of said bottom member to said first clamping arm.

13. The system of claim 9, wherein said body includes a medial member extending between first and second sides of said body, said first and second receptacles extending through said medial member.

14. The system of claim 13, wherein said body defines a first window between said first clamping arm and said medial member and a second window between said second clamping arm and said medial member, said first and second receptacles opening into each of said first and second windows, wherein said end portion of said first clamping arm forms a terminal end of said second receptacle between said first window and said first end of said body and said end portion of said second clamping arm forms a terminal end of said first receptacle between said second window and said second end of said body.

15. A spinal rod system, comprising:
   a connector including an elongate body extending along a central longitudinal axis between a first end and a second end, said body including:
      a bottom member extending between said first and second ends and between opposite sides of said body;
      a first clamping arm adjacent said first end defining a first receptacle with said bottom member, said first receptacle extending along a first longitudinal axis offset to a first side of said central longitudinal axis, said first clamping arm includes a first end portion extending from said first receptacle along said bottom member, said first end portion including a first pair of engaging members extending therethrough and engaging said bottom member, said first pair of engaging members being aligned along and extending transversely to said second longitudinal axis;
      a second clamping arm adjacent said second end defining a second receptacle with said bottom member, said second receptacle extending along a second longitudinal axis offset to a second side of said central longitudinal axis, said second clamping arm including a second end portion extending from said second receptacle along said bottom member, said second end portion including a second pair of engaging members extending therethrough and engaging said bottom member, said second pair of engaging members being aligned along and extending transversely to said first longitudinal axis;
      a medial member extending between said opposite sides of said body, said first and second receptacles extending through said medial member;
      a first window between said medial member and said first clamping arm in communication with said first and second receptacles;
      a second window between said medial member and said second clamping arm in communication with said first and second receptacles, wherein said bottom member extends through said first and second windows between said first and second ends and said opposite sides of said body;
   a first elongated rod axially received in said first receptacle of said connector and being engaged therein with said first clamping arm; and
   a second elongated rod axially received in said second receptacle of said connector and being engaged therein with said second clamping arm, wherein said first end portion of said first clamping arm forms a terminal end of said second receptacle between said first window and said first end of said body and said second end portion of said second clamping arm forms a terminal end of said first receptacle between said second window and said second end of said body.

16. The system of claim 15, wherein said bottom member includes first and second semi-cylindrical recessed portions extending along and at least partially defining respective ones of said first and second receptacles.

17. The system of claim 15, wherein said bottom member includes at least one window extending therethrough in communication with said first receptacle and at least one window therethrough in communication with said second receptacle.

* * * * *